United States Patent [19]

Nakamura et al.

[11] Patent Number: 4,463,197

[45] Date of Patent: Jul. 31, 1984

[54] METHOD FOR PURIFYING PHLOROGLUCIN

[75] Inventors: Makoto Nakamura, Ibaraki; Tsutomu Chiyoda, Toyonaka; Shinichi Hasegawa, Otsu, all of Japan

[73] Assignee: Sumitomo Chemical Company, Limited, Osaka, Japan

[21] Appl. No.: 443,691

[22] Filed: Nov. 22, 1982

[30] Foreign Application Priority Data

Dec. 1, 1981 [JP] Japan ................................ 56-193942

[51] Int. Cl.$^3$ .............................................. C07C 37/84
[52] U.S. Cl. .................................. 568/754; 568/753; 568/763; 568/768
[58] Field of Search ................ 568/763, 768, 753, 754

[56] References Cited

FOREIGN PATENT DOCUMENTS

| | | | |
|---|---|---|---|
| 12239 | 10/1956 | German Democratic Rep. | 568/768 |
| 1039636 | 4/1976 | Japan | 568/753 |
| 751598 | 6/1956 | United Kingdom | 568/768 |
| 1412308 | 11/1975 | United Kingdom | 568/754 |

*Primary Examiner*—Werren B. Lone
*Attorney, Agent, or Firm*—Stevens, Davis, Miller & Mosher

[57] ABSTRACT

A method for purifying phloroglucin wherein crude phloroglucin obtained by an acid-decomposition of 1,3,5-triisopropylbenzene trihydroperoxide in the presence of a solvent and removal of the formed acetone and the solvent by evaporation, is extraction-treated within a pH range of 7.5 to 12 in the coexistence of an aqueous alkali liquor of 4 to 25 times by weight based on the crude phloroglucin and an organic solvent of 0.05 to 6 times by weight based on said aqueous alkali liquor selected from ketones and esters which are separable from the aqueous alkali liquor, and after acidifying the separated aqueous alkali extract, the deposited crystal is recrystalized.

The phloroglucin is useful as a starting material of medicines and photosensitizers.

1 Claim, No Drawings

METHOD FOR PURIFYING PHLOROGLUCIN

The present invention relates to a method for purifying phloroglucin.

It is well known that 1,3,5-triisopropylbenzene trihydroperoxide (hereinafter referred to as THPO) obtained by the oxidation of 1,3,5-triisopropylbenzene (hereinafter referred to as TIP) is decomposed with an acid in the presence of a solvent to obtain phloroglucin.

Phloroglucin is used for various uses such as an intermediate for medicines, coupler for diazo photosensitive paper, stabilizing agent, crosslinking agent, reagent for analysis and the like, and its high-quality product is required.

Also, phloroglucin has a tendency to absorb oxygen in aqueous alkali solutions whereby phloroglucin itself deteriorates and colors. This tendency is particularly remarkable when the purity of phloroglucin is poor.

Now, phloroglucin produced by the acid-decomposition of THPO, as obtained by the oxidation of TIP, contains various impurities such as acetylphenols, carbinolphenols, isopropenylphenols, isopropylphenols, condensation products of carbinolphenols with phloroglucin, condensation products of phloroglucin with acetone and the like. It is therefore necessary to separate these impurities from the acid-decomposition product to purify phloroglucin. But impurities are similar to the intended phloroglucin in chemical structure and exhibit very similar physical properties to phloroglucin, and also phloroglucin has no boiling point, so that the separation of these impurities has been very difficult.

For this reason, the present inventors extensively studied a method for removing the impurities efficiently from the phloroglucin-containing reaction product obtained by the acid-decomposition of THPO in the presence of a solvent, thereby purifying phloroglucin advantageously. As a result of these studies, the present inventors have provided the method of the present invention.

According to the present invention, there is provided a method for purifying phloroglucin wherein crude phloroglucin obtained by an acid-decomposition of THPO in the presence of a solvent and removal of the formed acetone and the solvent from the resulting reaction product, is extraction-treated within a pH range of 7.5 to 12 in the coexistence of an aqueous alkali liquor of 4 to 25 times by weight based on the crude phloroglucin and an organic solvent of 0.05 to 6 times by weight based on said aqueous alkali liquor selected from ketones and esters which are separable from the aqueous alkali liquor, and after acidifying the separated aqueous alkali extract, the deposited crystal is recrystallized.

Next, the method of the present invention will be illustrated in detail.

In the method of the present invention, crude phloroglucin, a starting material for purification, is obtained by the acid-decomposition of THPO in the presence of a solvent and removal of the formed acetone and the solvent in advance by distillation, etc. from the resulting reaction product. As described later, however, when the solvent used in the acid-decomposition is the same as that used in the extraction treatment described below, it is not necessary to remove all of the solvent, but some required amounts may be left for use as a solvent for extraction.

The expression "removal of the formed acetone and the solvent" does not always mean absolute removal, but means removal of such a degree that there is no particular adverse effect on the subsequent treatments.

The crude phloroglucin above is extraction-treated in the coexistence of an aqueous alkali liquor and an organic solvent selected from ketones and esters which are separable from the liquor, to separate into the aqueous alkali solution layer containing phloroglucin and the organic solvent layer containing impurities.

The aqueous alkali liquor used herein consists of aqueous solutions obtained by dissolving common alkali substances such as sodium hydroxide, potassium hydroxide, lithium hydroxide, barium hydroxide, calcium hydroxide, sodium carbonate, potassium carbonate, ammonia, etc. in water. The amount of the aqueous alkali liquor used is 4 to 25 times by weight based on the weight of crude phloroglucin. The alkali concentration of the aqueous alkali liquor is an amount necessary to maintain the pH at the extraction-treatment at 7.5 to 12.

As specific examples of the ketones and esters separable from the aqueous alkali liquor, there are given for example ketones such as aliphatic ketones (e.g. methyl isobutyl ketone, methyl n-propyl ketone, methyl n-butyl ketone, diethyl ketone, ethyl n-butyl ketone), alkylketones (e.g. acetophenone) and cycloalkanones (e.g. cyclohexanone); and esters such as alkyl esters (e.g. ethyl acetate, n-propyl acetate, isopropyl acetate, n-butyl acetate, isobutyl acetate, methyl propionate, butyl propionate) and aromatic esters (e.g. methyl benzoate, ethyl benzoate, methyl salicylate). Of these, methyl isobutyl ketone, methyl n-propyl ketone, acetophenone, ethyl acetate, isopropyl acetate are preferably used.

Other solvents, for example, aliphatic hydrocarbons, aromatic hydrocarbons, alicyclic hydrocarbons, halogenated hydrocarbons, ethers and alcohols are not preferred in terms of separation effect.

The amount of the solvent used varies with extraction conditions such as the kind of extraction solvent, extraction temperature, etc., but generally, it is within a range of 0.05 to 10 times by weight, preferably 0.1 to 5 times by weight, based on the weight of the aqueous alkali liquor.

When the organic solvent used in the decomposition of THPO is the same as that used in the extraction treatment, a method may be employed in which, on removing said solvent from the decomposition product, the amount of distillate and the like are controlled so as to leave a required amount of solvent, and in which the residual solvent is used as extraction solvent.

The pH at the extraction treatment depends upon the extraction temperature, kind of solvent, etc., but it is within a range of generally 7.5 to 12, preferably 8 to 11.

It is sufficient for the extraction temperature to be not less than that at which solids such as crystals are not deposited during the extraction treatment. However, overly high temperatures are not desirable in terms of the stability of phloroglucin, and accordingly the temperature utilized is, in general, in the range of 10° to 100° C.

The extraction method is not particularly limited, and it is carried out as usual whether it is of a batchwise form or a continuous one. The extraction may be carried out optional times.

By this extraction treatment, phloroglucin is extracted with the aqueous alkali layer and impurities move to the organic solvent layer. By separating the latter layer, the impurities can be removed.

The aqueous liquor layer thus obtained is neutralized and then acidified with an acid to deposit phloroglucin crystals.

The acid used at this time is selected from common acids such as sulfuric acid, hydrochloric acid, acetic acid, carbonic acid, nitric acid, phosphoric acid and the like. Acidification is carried out with these acids until the pH of the acidified aqueous solution reaches 6 or less. The acidification temperature is generally 5° to 80° C., but finally, the temperature of the solution is cooled to about 0° C. to about 20° C. in order to separate the deposited crystals.

Thus, high-purity phloroglucin is obtained, but it is recrystallized in order to obtain a further high purity.

As the solvent for recrystallization, water is generally used. The crystallization itself is carried out by the usual methods, and generally, it is carried out by mixing the deposited crystal obtained above and a suitable amount of water, dissolving the crystal completely by heating to not less than 40° C., and cooling the solution to 0° to 20° C. to deposit crystals again, followed by filtration.

Thus, phloroglucin is obtained in high purity from the crude phloroglucin, but for the purpose of obtaining higher-purity products, it is more useful to use activated carbon together on the recrystallization. When activated carbon is used, the amount used is generally 0.001 to 10% by weight based on the weight of the aqueous solution.

Also, to use a reducing agent having a reducing power such as sodium hydrogen sulfite, sodium thiosulfate or sodium dithionite together with activated carbon is further useful in terms of prevention of coloration. In this case, the amount of reducing agent used is generally 10 to $10^4$ ppm as a concentration in the aqueous solution to which the agent is applied.

Further in the method of the present invention, to carry out the steps included in the method, i.e. extraction treatment, neutralization/acidification and recrystallization, particularly extraction treatment in nitrogen atmosphere is very useful from the standpoint of preventing phloroglucin from undergoing deterioration and coloration.

Thus, according to the present invention, phloroglucin can be purified in high purity from the crude phloroglucin obtained by the acid-decomposition of THPO.

Next, the present invention will be illustrated with reference to the following examples.

EXAMPLE 1

From a reaction product obtained by the acid-decomposition of THPO, as obtained by the oxidation of TIP, in the coexistence of methyl isobutyl ketone, the formed acetone and MIBK were removed to obtain crude phloroglucin containing 68% by weight of pure phloroglucin.

This crude phloroglucin was extraction treated under the extraction conditions set forth below using various solvents and an aqueous alkali liquor, and a partition ratio to the aqueous alkali liquor was examined. The results shown in Table 1 were obtained.

Extraction conditions:
Amount of aqueous alkali liquor: 11.5 times by weight (based on crude phloroglucin).
Kind of alkali: sodium hydroxide
Amount of solvent: 0.5 time by weight (based on aqueous alkali liquor).
pH at extraction: 8.5
Temperature at extraction: 60° C.

TABLE 1

| | Solvent | Partition ratio (wt. %) Phloroglucin | Impurities |
|---|---|---|---|
| Example | Methyl isobutyl ketone | 79.5 | 21.0 |
| | Ethyl acetate | 80.8 | 28.0 |
| Comparative Example | Amyl alcohol | 70.5 | 35.0 |
| | Isopropyl ether | 93.4 | 85.0 |
| | n-Bytyl ether | 94.7 | 89.5 |
| | Dichloroethane | 90.9 | 93.0 |
| | Toluene | 95.1 | 99.0 |
| | Cyclohexane | 93.5 | 99.5 |
| | o-Dichlorobenzene | 94.5 | 99.5 |
| | Difluorotetrachloroethane | 94.7 | 100 |
| | n-Hexane | 90.5 | 99.5 |

EXAMPLE 2

One hundred grams of the crude phloroglucin obtained in Example 1 is dissolved in 270 g of methyl isobutyl ketone and 540 g of water, and a 45 wt.% aqueous sodium hydroxide solution is added at 40° C. with stirring until the pH reaches 9. Thereafter, the solution is allowed to stand to separate into two layers, and the aqueous alkali layer is separated from it. To this aqueous alkali layer is added 160 g of fresh methyl isobutyl ketone. After stirring, the mixed solution is allowed to stand to separate into two layers, and the aqueous alkali layer is separated from it. This aqueous layer is acidified at 40° C. with stirring with addition of a 30 wt. % aqueous sulfuric acid solution until the pH reaches 2.5. All the operations described above are carried out under a nitrogen atmosphere. The acidified solution is cooled to 15° C., and the deposited crystal is filtered off.

To the crystal obtained is added 300 g of water, and the crystal is dissolved by heating to 70° to 75° C. To this aqueous solution are added 1.8 g of activated carbon and 0.002 g of sodium hydrogen sulfite, followed by thorough stirring.

Thereafter, the solution is filtered hot at the same temperature to remove activated carbon, the filtrate is cooled to 15° C. with stirring, and the deposited crystal is filtered off and dried to obtain colorless phloroglucin crystal. The purity after drying was 98% or more (anhydrous product), and m.p. was 217°–219° C.

The methyl isobutyl ketone layer separated by extraction treatment, the filtrate after acidification and the filtrate after recrystallization are combined, and to the mixture is added a 45 wt. % aqueous sodium hydroxide solution at 40° C. with stirring to make the pH 9.3. The solution is then allowed to stand to separate into two layers. The same acidification and recrystallization as above are applied to the separated aqueous alkali layer to recover phloroglucin.

By the treatment above, the purification yield of phloroglucin was 90%.

The crude phloroglucin was purified in completely the same manner as in the foregoing example except that activated carbon and sodium hydrogen sulfite were not used. As a result, the same purity and yield as above were obtained except that the crystal obtained was slightly colored a pale yellow.

EXAMPLE 3

Purification of the crude phloroglucin was carried out in completely the same condition and method as in Example 2 except that ethyl acetate was used as extraction solvent in place of methyl isobutyl ketone.

The phloroglucin obtained had a purity of 98.0% or more (anhydrous product) and a melting point of 217°–219° C. The purification yield was 88%.

COMPARATIVE EXAMPLE 1

One hundred grams of the crude phloroglucin obtained in Example 1 was dissolved in 540 g of water at 70° to 75° C. At this time, a tarry matter formed the lower layer. After removing the tarry matter, the solution was cooled to 15° C. to deposit crystals.

After solid/liquid separation, for the purpose of recrystallization, the crystal was dissolved in 540 g of water at 70° to 75° C., and after separating a small amount of tarry matter, the solution was cooled to 15° C. to obtain phloroglucin crystals.

Dissolution and recrystallization were carried out once again to obtain phloroglucin crystals. The purity of the phloroglucin after thus carrying out recrystallization three times was 85.3% (anhydrous product).

What is claimed is:

1. A method for purifying crude phloroglucin obtained by an acid-decomposition of 1,3,5-triisopropylbenzene trihydroperoxide in the presence of a solvent followed by evaporation to remove the acetone formed and the solvent, said method comprising the steps of:
   (A) extraction-treating the crude phloroglucin with an aqueous alkali liquor in an amount of 4 to 25 times by weight based on the weight of crude phloroglucin and an organic solvent selected from the group consisting of ketones and esters that are seperable from the aqueous alkali liquor in an amount of 0.05 to 6 times by weight based on the weight of the alkali liquor to form an aqueous alkali extract and an organic solvent extract, said extraction treatment being conducted at a temperature of 10° to 100° C. and a pH of 7.5 to 12;
   (B) separating the organic solvent extract from the aqueous alkali extract;
   (C) acidifying the separated aqueous alkali extract to obtain phloroglucin crystals; and
   (D) subjecting the phloroglucin crystals obtained in step (C) above to a recrystallization treatment in order to further purify the phloroglucin.

* * * * *